United States Patent [19]

Wu

[11] Patent Number: 6,087,089

[45] Date of Patent: *Jul. 11, 2000

[54] PEROXIDE AND CHLORINE TEST STRIP

[75] Inventor: Wen H. Wu, Elkhart, Ind.

[73] Assignee: Integrated Biomedical Technology, Inc., Elkhart, Ind.

[*] Notice: This patent is subject to a terminal disclaimer.

[21] Appl. No.: 09/088,741

[22] Filed: Jun. 2, 1998

Related U.S. Application Data

[63] Continuation-in-part of application No. 08/969,026, Nov. 12, 1997.

[51] Int. Cl.[7] .............................. C12Q 1/00; C12Q 1/22; C12Q 1/28
[52] U.S. Cl. .................................. 435/4; 435/31; 435/28; 435/970; 423/582
[58] Field of Search .................................. 435/4, 31, 28, 435/970; 423/582

[56] References Cited

U.S. PATENT DOCUMENTS

| | | | |
|---|---|---|---|
| 3,814,668 | 6/1974 | Blake et al. | 195/103.5 C |
| 4,098,575 | 7/1978 | Matsushita | 435/4 |
| 4,181,500 | 1/1980 | Cowsar et al. | 23/230 B |
| 4,303,753 | 12/1981 | Lam | 435/14 |
| 4,597,975 | 7/1986 | Woodward et al. | 435/4 |
| 4,621,049 | 11/1986 | Wang | 435/14 |
| 4,755,472 | 7/1988 | Ismail et al. | 435/4 |
| 4,900,682 | 2/1990 | Fischer et al. | 435/4 |
| 4,992,296 | 2/1991 | Gibson | 427/2 |
| 5,217,691 | 6/1993 | Greene et al. | 422/56 |
| 5,648,075 | 7/1997 | Kessler et al. | 435/4 |
| 5,906,916 | 5/1999 | Wu | 435/4 |

OTHER PUBLICATIONS

Zwick, "Poly(vinyl alcohol)—Iodine complexes," *Journal of Applied Polymer Science*, vol., 9, pp. 2393–2424 (1965).
Bottle Label, Renalin Perassay 500, Renal Systems, Minneapolis, MN.
Package insert—Renalin Perassay 500 Reagent Strip, Renal Systems, Minneapolis, MN, (1998).

*Primary Examiner*—Louise N. Leary
*Attorney, Agent, or Firm*—Marshall, O'Toole, Gerstein, Murray & Borun

[57] ABSTRACT

A composition, method, and test device for quantitatively determining the oxidant concentration of a test sample are disclosed. The test device includes a test pad having a suitable carrier matrix incorporating an indicator reagent composition capable of interacting with an oxidant to produce a detectable and measurable response for oxidant over a wide concentration range of oxidant. An indicator reagent composition contains: (a) an iodide salt, (b) a buffer, and (c) a water-soluble polymer, preferably a cellulose-based polymer. An indicator reagent composition is incorporated into a carrier matrix, like filter paper, to provide a test pad useful in a dry phase oxidant assay of a test sample, especially for test samples containing a high concentration of oxidant, like chlorine or a peroxide.

34 Claims, No Drawings

PEROXIDE AND CHLORINE TEST STRIP

CROSS-REFERENCE TO RELATED APPLICATIONS

This is a continuation-in-part application of U.S. patent application Ser. No. 08/969,026, filed Nov. 12, 1997, pending.

FIELD OF THE INVENTION

The present invention relates to a composition, method, and test device for determining the peroxide or chlorine concentration of a test sample. More particularly, the present invention relates to a method and test device for assaying a liquid test sample for peroxide or chlorine concentration over the range of 0% to greater than 4%, by weight, by using an improved indicator reagent composition. The indicator reagent composition undergoes a detectable and measurable response upon contact with a test sample containing a peroxide or chlorine. Contrary to prior compositions, the present indicator reagent compositions have the advantage of quantitatively measuring the high range of peroxide or chlorine concentration without diluting the test sample.

BACKGROUND OF THE INVENTION

The use of peroxide or chlorine as a sanitizer or disinfectant for various types of equipment, like food processing equipment and medical equipment, such as a hemodialysis unit, is common. Because the amount of peroxide or chlorine in an aqueous solution relates directly to the disinfecting or sanitizing activity thereof, a test which rapidly and accurately measures peroxide or chlorine concentration is important.

The use of a peroxide, like hydrogen peroxide or peracetic acid, or chlorine as a disinfectant for medical equipment is widespread because of their low cost, convenience, and effectiveness as an antiseptic agent in relatively low concentrations. For example, peroxides and chlorines are used as a disinfectant in a substantial number of hemodialysis centers. Such oxidants are used in hemodialysis centers to sanitize hemodialysis units because oxidants are an effective and economical sanitizing agent. It also is important to clean and disinfect a hemodialysis unit between each dialysis session to prevent pathogen contamination from patient to patient.

Chlorine is a commonly used disinfectant and sanitizer in medical and other applications. Chlorine typically is available as an aqueous solution containing 5.25% sodium hypochlorite, which is equivalent to about 50,000 ppm free available chlorine. The 5.25% sodium hypochlorite solution is diluted with water to a suitable use level, such as about 250 to about 5000 ppm free available chlorine, for disinfection.

Chlorine also is a very toxic compound that can cause hemolysis even when only a trace amount of chlorine diffuses from the hemodialysis unit into the blood of an individual. Therefore, a hemodialysis unit must be rinsed sufficiently free of chlorine such that a potentially toxic amount of chlorine does not remain in the hemodialysis unit. Trace amounts of chlorine also can adversely affect filtration membranes of the hemodialysis unit.

When a sanitizing solution is used in medical or food processing equipment, two critical oxidant, i.e., peroxide or chlorine, levels must be monitored. First, the disinfectant concentration, either peroxide or chlorine, must be sufficiently high to perform a sanitizing or disinfecting function, i.e., at least about 1000 ppm (parts per million) peroxide or chlorine is needed to effectively sanitize equipment. During the sanitizing process, the sanitizing solution is assayed periodically to ensure that sufficient active disinfectant is present to sanitize the equipment.

After the sanitizing function is completed, and before reuse, the equipment is rinsed with water to flush residual oxidant from the equipment. The rinse water also is assayed for active oxidants to ensure that the level of residual oxidants is below the maximum allowable level.

Presently, there is one type of commercial assay system for assaying hemodialysis units for peroxide concentration. The assay is semiquantitative and merely indicates that sufficient peroxide is present to sanitize the equipment, or that the peroxide is below this sanitizing level. No other quantitative information is available from the assay. This assay relies on a color transition formed by a starch iodine complex.

Assays for chlorine are common, and also are based on a starch iodine complex color transition. Prior chlorine assays are disclosed in Rupe et al. U.S. Pat. No. 4,092,115 and Ramana et al. U.S. Pat. No. 5,491,094. Further, examples of prior disclosures relating to assaying for chlorine include Storm U.S. Pat. No. 3,718,605; Reiss U.S. Pat. No. 4,938,926; Ross, Jr. et al. U.S. Pat. No. 4,049,382; Frant U.S. Pat. No. 5,300,442; Harp U.S. Pat. No. 5,362,650; O'Brien et al. U.S. Pat. No. 4,904,605; and J. D. Johnson et al., *Analytical Chemistry*, 40(13), pages 1744–1750 (1969).

In addition, there are two types of commercial assay systems for assaying hemodialysis units for chlorine. One assay utilizes tablets or dry powder, and the other utilizes dry chemistry dip strips. Each assay has advantages and disadvantages, and neither assay satisfies the different testing requirements needed for a hemodialysis unit.

The tablet method has good sensitivity (e.g., 0.1 ppm) and is less expensive per assay. However, the tablet method is more cumbersome to perform and requires more technician time. The dry chemistry test strips usually are not as sensitive as the tablet method and can cost more per test. Nevertheless, the strip test is very easy and convenient, particularly when operating a mobile hemodialysis unit. In most hemodialysis centers, the test strip is used as a screening test for residual chlorine, whereas the tablet method is used for more critical water testing. Because of the differences in test requirements, most hemodialysis centers are forced to stock both the tablet and dry chemistry test systems.

A starch-iodide solution had been used as an indicator for oxidation-reduction (redox) titrations for decades. The starch iodine complex has a sharp and intense color transition, turning from colorless for the iodide ion to dark blue for the starch iodine complex. A starch iodine color transition, therefore, is used mainly as an end point indicator. The color intensity of the starch iodine complex formation is so great that the color transition from iodide to iodine does not allow a quantitative distinction between different concentrations of an oxidant, like peroxide or chlorine, present in a test sample. Consequently, there was little to no impetus to use formation of a starch iodine complex in a quantitative calorimetric determination of an oxidant in a test sample, especially at high oxidant concentrations.

To be useful in a quantitative assay, color transitions must be differentiable and related to the concentration of the analyte of interest. Therefore, it is necessary to find a color-forming complex that undergoes a color transition of weaker intensity than the starch iodine complex. The identity of this less intensely colored complex has evaded workers in the art, especially with respect to an assay for a peroxide or chlorine in a high concentration range of about 0.1% to greater than about 4% peroxide, or about 0.025% to greater than about 0.5% chlorine, by weight of the test sample.

The search for a compound that binds to iodine, and forms a colored complex suitable for use in a quantitative assay for an oxidant, like peroxide or chlorine, has not been successful until the present disclosure. For example, M. M. Zwick, *Journal of Applied Polymer Science*, Vol. 9, pp. 2393–2424 (1965), discloses formation of blue color complex of iodine and polyvinylalcohol. The Zwick publication discloses a structural requirement and mechanism for the formation of an iodine-polymer complex, but does not address or consider a relationship between color intensity of the complex and iodine concentration. Furthermore, the Zwick publication fails to suggest any utility of a colored iodine-polymer complex, in particular in an assay for oxidant concentration in aqueous solution.

Various patents are directed to the starch iodine complex as the indicator in an assay of a test sample. U.S. Pat. Nos. 3,814,668 and 4,303,753 disclose the use of potassium iodide as a redox indicator in the presence of polyvinylpyrrolidone (PVP) for detection of glucose in urine. Such an indicator system is used in the DIASTIX® urine glucose test strip, marketed by Bayer Diagnostics, Elkhart, Ind. The maximum color intensity for glucose concentration is 2000 mg/dL, which is stoichiometrically equivalent to 111 mM hydrogen peroxide, and which, in turn, is equivalent to 37771 mg/L or 0.37% by weight of hydrogen peroxide. Because only a fraction of glucose in the test sample is actually reacted to release hydrogen peroxide, the indication is responding to an actual peroxide concentration that is probably much less than the calculated level of 0.37% by weight.

Similarly, U.S. Pat. No. 4,621,049 discloses the use of iodide ion and PVP as an indicator in an assay for measuring a glucose concentration as high as 10,000 mg/dL. In such a assay, however, the ability to measure a high range of glucose is achieved by modulating enzyme reactivity through a borate buffer at an alkaline pH, as disclosed in the U.S. Pat. No. 5,217,691. The indicator system, again, is responding to only a fraction of glucose in the test sample. Therefore, the indicator used in DIASTIX® is responding only to low levels of hydrogen peroxide, and does not disclose or suggest an ability to respond to a peroxide concentration of 0.1% by weight, or higher, or a chlorine concentration of 0.025% by weight, or higher. Other patents directed to iodide/iodine indicators are U.S. Pat. Nos. 4,181, 500 and 4,992,296.

To date, no known single assay is available to assay a wide oxidant concentration range because the large oxidant concentration difference makes detection and differentiation between concentration levels difficult. The present invention is directed to (a) providing an assay for peroxide that is capable of measuring peroxide concentration over the range of 0% to about 4%, and especially about 0.1% to about 4%, by weight, without diluting the test sample, and (b) providing an assay for chlorine that is capable of measuring chlorine concentration over the range of 0% to about 1%, and especially about 0.025% to about 0.75%, by weight (i.e., 0 to 10,000 ppm, and 250 to about 7500 ppm, respectively), without diluting the test sample.

The present invention, therefore, is directed to an assay method and device that can be used to test samples containing wide ranges of oxidant concentrations, without diluting the sample. As illustrated hereafter, the present test strips have a good sensitivity and a wide detection range with a continuous color response from 0.1% to over 4%, by weight, peroxide or, from 0.025% to over 0.75% chlorine, without diluting the test sample.

The present method of assaying for peroxide or chlorine in an aqueous test sample yields trustworthy and reproducible results by utilizing an indicator reagent composition that undergoes a color transition in response to oxidant concentration, and not as a result of a competing chemical or physical interaction, such as a preferential interaction with another test sample component. Additionally, the method and composition utilized in the present assay does not adversely affect or interfere with any other test reagent pads that are present on a multiple test pad strip.

In accordance with the present invention, an indicator reagent composition can be incorporated into a carrier matrix to provide sufficient sensitivity and color differentiation to assay for peroxide concentration over the range of 0% to greater than about 4%, or chlorine concentration over the range of 0% to greater than about 1%, by weight, without sample dilution. In addition, although dry phase test strips have been used to assay for peroxide or chlorine concentration, no dry phase test strip has been used to quantitatively assay an undiluted test sample for peroxide or chlorine at the high concentration range.

SUMMARY OF THE INVENTION

In brief, the present invention is directed to a new and improved composition, test device, and method of determining the peroxide or chlorine concentration of a test sample. A device includes a test pad comprising a suitable carrier matrix incorporating an indicator reagent composition capable of interacting with a peroxide or chlorine to produce a detectable response to oxidant concentration. A carrier matrix of the test pad comprises a bibulous material, such as filter paper; a nonbibulous material, such as a strip, layer, or membrane of a polymerized material; or a mixture thereof. An indicator reagent composition is homogeneously incorporated into the carrier matrix, and the carrier matrix then holds the indicator reagent composition homogeneously throughout the carrier matrix while maintaining carrier matrix penetrability by the test sample.

More particularly, the present invention is directed to a method of assaying for the oxidant, i.e., peroxide or chlorine, content of aqueous test samples by utilizing a new indicator reagent composition. It has been demonstrated that a reagent composition including: (a) an iodide salt, (b) a buffer, like a polycarboxylic acid, and (c) a water-soluble polymer, and preferably a cellulose-based polymer, affords sufficient sensitivity to test sample oxidant content, and a sufficient color differentiation between test samples having a different peroxide content over the range of 0% to greater than about 4%, and particularly about 0.1% to greater than about 4%, by weight, or a different chlorine content over the range of 0% to greater than about 1%, and particularly about 0.025% to greater than about 0.75%, by weight.

In accordance with an important feature of the present invention, an accurate and reliable quantitative determination for peroxide or chlorine in an undiluted test sample is achieved because the indicator reagent composition undergoes a differentiable color transition in response to the oxidant content of the test sample, even at a high concentration of oxidant. By utilizing an indicator reagent composition of the present invention, the quantitative assay for oxidant in liquid test samples is more sensitive and accurate because the indicator reagent composition is able to detect, and differentiate between, high levels of peroxide or chlorine present in a test sample.

Therefore, one aspect of the present invention is to provide a method and composition for quantitatively determining the oxidant concentration of an aqueous liquid. The composition interacts with the peroxide or chlorine to produce a change in color of a test device that is indicative of the peroxide or chlorine concentration of the test sample.

Another aspect of the present invention is to provide a method of assaying aqueous test samples, said method having sufficient sensitivity and sufficient visual color resolution to allow differentiation between, and the quantitative measurement of, test samples having different oxidant concentrations.

Yet another aspect of the present invention is to provide a sensitive method of assaying undiluted test samples for peroxide concentration over the range of 0% to greater than about 4% by weight peroxide. The present method is especially useful in the detection of a high concentration of peroxide, i.e., about 0.1% to greater than about 4%, by weight of the test sample.

Another aspect of the present invention is to provide a method of assaying undiluted test samples for chlorine concentration over the range of 0% to greater than about 1%, by weight of the test sample (i.e., 0 to greater than 10,000 ppm). The present invention is especially useful in the detection of a high concentration of chlorine, i.e., about 0.025% to about 0.75%, by weight, of the test sample to (i.e., about 250 to about 7500 ppm) chlorine, and most preferably useful at a concentration of about 0.02% to about 0.5%, by weight, of the test sample (i.e., about 250 to about 5000 ppm).

Another aspect of the present invention is to provide an indicator reagent composition that interacts with either peroxide or chlorine and undergoes a visually or instrumentally differentiable color transition to allow the determination of peroxide or chlorine concentration of a test sample.

Another aspect of the present invention is to provide a method of assaying for the oxidant content of a liquid test sample by incorporating an indicator reagent composition into a dry phase detection device, wherein the indicator reagent composition comprises: (a) an iodide salt, (b) a buffer, (c) a water-soluble polymer, preferably a cellulose-based polymer, and (d) a suitable carrier.

Still another aspect of the present invention is to provide a new and improved method of assaying for the oxidant content of an aqueous test sample by utilizing a test device, including a carrier matrix, said carrier matrix comprising a bibulous matrix, like filter paper, or a nonbibulous matrix, like a glass fiber or a layer of a permeable polymeric material, and said carrier matrix having incorporated therein an indicator reagent composition capable of interacting with peroxide or chlorine present in the test sample, to provide a color transition that can be correlated to the oxidant concentration of the test sample.

A further aspect of the present invention is to provide an improved dry phase test strip that incorporates an indicator reagent composition comprising an iodide salt, a buffer, and a water-soluble polymer, into the carrier matrix, and thereby provide a quantitative assay for the peroxide or chlorine content of a test sample.

The above and other aspects and advantages and novel features of the present invention will become apparent from the following detailed description of the preferred embodiments.

DETAILED DESCRIPTION OF THE PREFERRED EMBODIMENTS

In accordance with the method of the present invention, a quantitative assay of aqueous test samples for oxidant content, and especially high concentrations of a peroxide or chlorine, is accomplished by utilizing an indicator reagent composition that includes (a) an iodide salt, (b) a buffer, and (c) a water-soluble polymer, preferably a cellulose-based polymer. By employing an indicator reagent composition of the present invention, sufficient sensitivity and sufficient visual color differentiation between test samples of different peroxide or chlorine content is achieved. In accordance with the method of the present invention, undiluted test samples having (a) a peroxide content of 0% to greater than about 4%, and particularly about 0.1% to greater than about 4%, by weight of the test sample, or (b) a chlorine content of 0% to greater than 1%, and particularly about 0.025% to greater than 1%, by weight of the test sample, can be measured and differentiated.

To achieve the full advantage of the present invention, the method and composition are employed in dry phase, test pad assays to determine the oxidant concentration of aqueous test samples. A dry phase test strip, including a test pad comprising a carrier matrix incorporating an indicator reagent composition of the present invention, allows the rapid quantitative assay of undiluted test samples by visual means.

In particular, the present invention allows determination of the peroxide or chlorine concentration of a test sample by the visual color change of a test pad on a test strip resulting from contact between the test strip and the test sample. Peroxide or chlorine concentration of the test sample is determined by correlating the detected color change to the peroxide or chlorine concentration of the test sample. The test strip includes a test pad comprising an inert carrier matrix incorporating an indicator reagent composition. The present composition and method allow the rapid calorimetric determination of the oxidant concentration of a test sample, and especially high peroxide concentrations.

Previous assay methods employed compositions that were unable to distinguish between aqueous solutions containing different concentrations of oxidant above about 0.1%, by weight, peroxide, or 0.025%, by weight, chlorine. The prior compositions utilized starch as a polymer, which forms a complex with iodine having a high color intensity, thereby making differentiation between color transitions, and oxidant concentration, difficult to impossible. In contrast, the present method measures oxidant content by utilizing an indicator reagent composition containing a water-soluble polymer that forms a complex with iodine having a weaker color intensity than a starch iodine complex, such that color transitions resulting from different oxidant concentrations can be differentiated and quantified.

One component of the present indicator reagent composition is the iodine indicator. The oxidant in the test sample reacts with iodide ion to form iodine. The iodine then is available to complex with a water-sojuble polymer that also is present in the indicator reagent composition.

Therefore, the indicator reagent composition contains an iodide salt, and typically potassium iodide. However, any water-soluble iodide salt having a cation that does not interfere with the assay for an oxidant can be used. Examples of other iodide salts are sodium iodide and lithium iodide.

In accordance with an important feature of the present invention, the iodine-polymer complex undergoes a color transition through various detectable and measurable degrees and intensities of color such that the degree and intensity of the color transition can be correlated to the concentration of oxidant in a test sample. In accordance with another important feature of the present invention, the indicator reagent composition undergoes a differentiable color transition at high oxidant concentrations, and, therefore, it is unnecessary to dilute the test sample. The ability to assay an undiluted test sample eliminates a common source of error from the assay.

The iodide salt typically is present in the indicator reagent composition in an amount of about 1% to about 4%, and preferably in an amount of about 1.5% to about 3%, by weight of the indicator reagent composition. To achieve the full advantage of the present invention, the iodide ion is present in an amount of about 1.75% to about 2.75%, by weight of the indicator reagent composition. In general, however, the amount of iodide salt included in the indicator reagent composition is limited only in that the composition undergoes a detectable color transition in proportion to the concentration of peroxide or chlorine in a test sample.

In accordance with an important feature of the present invention, it was found that iodine can bind to polymers other than starch to form a complex that is weaker than a starch iodine complex, and accordingly generates a weaker color transition. Such iodine-polymer complexes of the present invention can be used to detect and quantify the amount of peroxide or chlorine in a test sample.

It was found that iodine can bind with water-soluble polymers, and especially cellulose-based polymers, to form a color complex having a reddish-brown color. The color intensity and hue is related to the identity of the water-soluble polymer present in the iodine-polymer complex. Therefore, by proper selection of a water-soluble polymer, or mixture of polymers, it is possible to generate a scale of differentiable colors that correlate to a specific concentration range of oxidant.

In searching for a polymer that forms a weak iodine/polymer complex, and having weaker color intensity than an iodine-starch complex, it was surprising to find that iodine complexes with water-soluble polymers, such as hydroxypropylcellulose, to form a reddish-brown color. In the presence of an excess amount of polymer, iodine, which is formed by oxidation of iodide ion by an oxidant, like peroxide or chlorine, forms various degrees of reddish-brown color corresponding to the concentration of oxidant in a test sample. The color transitions then can be used to quantify the concentration of oxidant in the test sample by correlating the color transition to known concentrations of oxidant.

Therefore, in addition to an iodide salt, the indicator reagent composition contains a water-soluble polymer. The water-soluble polymer is a nonionic or anionic polymer, and preferably is a cellulose-based polymer. However, other water-soluble polymers, such as polyvinylpyrrolidone, also can be used as the polymer in a present indicator reagent composition. In preferred embodiments, the indicator reagent composition contains a mixture of cellulose-based polymers. In especially preferred embodiments, the indicator reagent composition contains a mixture of cellulose-based polymers, and an additional water-soluble polymer.

The water-soluble polymer is present in the indicator reagent composition in an amount of about 0.1% to about 5%, and preferably about 0.2% to about 3%, by weight of the indicator reagent composition. To achieve the full advantage of the present invention, the water-soluble polymer is present in the indicator reagent composition in an amount of about 0.5% to about 2.5%, by weight of the composition.

The preferred water-soluble polymers are cellulose-based polymers. In most preferred embodiments, the indicator reagent composition contains a mixture of water-soluble polymers to achieve a broad range quantitative assay, and particularly a high range quantitative assay, for oxidant. A mixture of water-soluble polymers also can provide an indicator reagent composition that responds to a specific oxidant concentration range.

The water-soluble, cellulose-based polymers are derivatives of cellulose wherein hydroxy groups on the sugar moiety of cellulose are modified with a short chain alkyl (i.e., $C_1$–$C_4$), alkyl alcohol, or alkyl carboxylic acid. Examples of some common cellulose modifications are replacing a portion of the hydroxy groups with methyl, hydroxymethyl, hydroxyethyl, hydroxyethylmethyl, hydroxypropyl, hydroxypropylmethyl, or carboxymethyl groups, for example.

The color intensity of an iodine-polymer complex is inversely proportional to the number of carbon atoms in the modifying moiety. For example, a cellulose-based polymer having hydroxyethyl groups forms a darker brown color than a cellulose-based polymer having a hydroxypropyl group. Accordingly, color intensity is related to the hydrophilicity of the polymer. For example, hydroxyethylcellulose is soluble only in water, but not in organic solvents, whereas hydroxypropylcellulose is soluble in both water or organic solvent. Carboxymethylcellulose is highly soluble in water, and forms dark brown color with iodine.

Examples of water-soluble cellulose-based polymers useful in the present invention include, but are not limited to, methylcellulose, hydroxymethylcellulose, hydroxyethylcellulose, hydroxyethylmethylcellulose, hydroxypropylcellulose, hydroxypropylmethylcellulose, carboxymethylcellulose and salts thereof, hydroxybutylcellulose, cellulose acetate, carboxymethylhydroxyethylcellulose, hydroxybutylmethylcellulose, and mixtures thereof. As illustrated hereafter, a blend of two or more water-soluble cellualose-based polymers provides a more intense color transition in response to peroxide or chlorine, and gives a wider color response to oxidant concentrations.

In addition to cellulose-based polymers, other water-soluble polymers can be used in the method and composition of the present invention. Such water-soluble polymers are nonionic or anionic in character. Examples of useful water-soluble polymers include, but are not limited to, polyvinylpyrrolidone, hydrolyzed polyvinylpyrrolidone, poly(vinyl alcohol), poly(vinyl acetate), vinyl acetatevinyl alcohol copolymers, polyvinyloxazolidone, polyvinylmethyloxazolidone, co-polymers of vinylpyrrolidone and a vinyl amide of γ-amine butyric acid, polyacrylic acid polymers, polyacrylic acid copolymers, partially or fully neutralized salts of polyacrylic acid polymers and polyacrylic acid copolymers, poly(methacrylic acid), poly (methacrylamide), poly(N,N-dimethylacrylamide), poly(N-isopropylacrylamide), poly(N-acetamidoacrylamide), poly (N-acetamidomethacrylamide), acrylic interpolymers of polyacrylic acid with poly(methacrylic acid), polyacrylic acid with poly(methacrylamide), polyacrylic acid with methacrylic acid, polyoxypropylenepolyoxyethylene block polymers having one of the following structures:

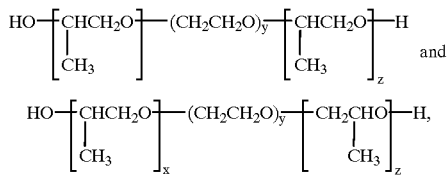

wherein x and z, independently, are an integer from about 4 to about 30, and y is an integer from about 4 to about 100, polyacrylamide, copolymers of acrylamide, acrylamide/sodium acrylate copolymers, acrylate/acrylamide copolymers, acrylate/ammonium methacrylate copolymers, acrylate/diacetoneacrylamide copolymers, acrylic/acrylate copolymers, adipic acid/dimethylaminohydroxypropyl diethylenetriamine copolymers, ammonium acrylate copolymers, ammonium styrene/acrylate copolymers, ammonium vinyl acetate/acrylate copolymers, aminomethylpropanol acrylate/diacetoneacrylamide copolymers, aminomethylpropanediol acrylate/diacetoneacrylamide copolymers, butyl benzoic acid/phthalic anhydride/trimethyolethane copolymers, diethylene glycolamine/epichl-orohydrin/piperazine copolymers, ethylene/vinyl alcohol copolymers, ethyl esters of polyethylenimines, isopropyl ester of methyl vinyl ether/maleic anhydride copolymers, melamine/formaldehyde resin, methoxyethylene glycol/dodecyl glycol copolymers, octadecene/maleic anhydride copolymers, octylacrylamide/acrylate/butylaminoethyl methacrylate copolymers, octylacrylamide/acrylate copolymers, polyethylene glycol/dodecyl glycol copolymers, polyethyleneimrine, phthalic anhydride/glycerin/glycidyl decanoate copolymers, metal salts of polyacrylic acid, metal salts of methyl vinyl ether/maleic anhydride copolymers, vinylpyrrolidone/eicosene copolymers, vinylpyrrolidone/ethyl methacrylate/methacrylic acid copolymers, vinylpyrrolidone/hexadecene copolymers, vinylpyrrolidone/vinyl acetate copolymers, polyvinypyrrolidone/vinyl acetate/itaconic acid copolymers, sodium acrylate/vinyl alcohol copolymers, sodium polymethacrylate, sodium polystyrene sulfonate, sodium styrene/acrylate/polyethylene glycol-10 dimaleate copolymers, sodium styrene/polyethylene glycol-10 maleate/nonoxynol-10 maleate/acrylate copolymers, styrene/acrylamide copolymers, styrene/acrylate/ammonium methacrylate copolymers, styrene/maleic anhydride copolymers, styrene/polyvinyloxazolidone copolymers, urea formaldehyde polymers, urea/melamine/formaldehyde polymers, vinyl acetate/crotonic acid copolymers, vinyl alcohol copolymers, and mixtures thereof.

In addition to the iodide salt and water-soluble polymer, the indicator reagent composition also contains a buffer. In accordance with an important feature of the present invention, the buffer buffers the indicator reagent composition at a pH of about 2 to about 9, and preferably about 4 to about 7. To achieve the full advantage of the present invention, the buffer buffers the indicator reagent composition at a pH of about 5 to about 6.5.

The identity of the buffer is not particularly limited, as long as the indicator reagent composition is buffered at a pH of about 2 to about 9. Therefore, useful buffers include, but are not limited to, polycarboxylic acids, phosphate, borate, acetate, and mixtures thereof. Preferred buffers are polycarboxylic acids, and especially polycaroxylic acids wherein the carboxyl groups are separated by two to five carbon atoms. Examples of useful polycarboxylic acid buffers include, but are not limited to, citric acid, succinic acid, lactic acid, and ketoglutaric acid. The concentration of buffer in the composition typically is about 1%, to about 15%, and preferably about 5% to about 12%, by weight, of the composition.

In addition to the iodide salt, the water-soluble polymer, and the buffer, the indicator reagent composition also can contain optional ingredients. For example, one optional ingredient is a surfactant, in particular an anionic surfactant or a nonionic surfactant. The surfactant improves the ability of the test sample to wet the carrier matrix, and the surfactant also improves the stability of the color transition of the indicator in response to oxidant.

The surfactant is present in the indicator reagent composition in an amount of 0% to about 1.5%, and preferably about 0% to about 1%, by weight of the composition. To achieve the full advantage of the present invention, the surfactant is present in an amount of about 0% to about 0.5% by weight of the composition.

Useful nonionic surfactants include, but are not limited to, an othoxylated polysorbate, e.g., polysorbate 20 through polysorbate 85, an ethoxylated alcohol, e.g., a $C_{10}$ to $C_{22}$ alcohol ethoxylated with about 10 to about 25 moles of ethylene oxide, an ethoxylated phenol, i.e., an ethoxylated octylphenol, nonylphenol, or dodecylhenol with about 8 to about 30 moles of ethylene oxide, a polyethylene glycol, e.g., PEG-8 through PEG-40, a polypropylene glycol, e.g., PPG-9 through PPG-34, an ethylene glycol-propylene glycol copolymer, e.g., a poloxamer, a polybutylene glycol, and similar nonionic surfactants, and mixtures thereof. In general, a useful nonionic surfactant has an HLB value of about 6 to about 25.

Anionic surfactants useful in the present invention are not particularly limited. Usually, the anionic surfactant includes a hydrophobic moiety, such as a carbon chain including about eight carbon atoms to about 30 carbon atoms, and particularly about twelve carbon atoms to about twenty carbon atoms; and further includes a hydrophilic moiety, such as sulfate, sulfonate, carbonate, phosphate, or carboxylate. Often, the hydrophobic carbon chain is etherified, such as with ethylene oxide or propylene oxide, to impart a particular physical property or reduced surface tension, to the anionic surfactant.

The anionic surfactants are well known, and can be a fatty acid, a salt of a fatty acid, an ethoxylated fatty acid, or a salt of an ethoxylated fatty acid, for example. Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkyloxy alkane sulfonates, alkyl arylsulfonates, alkyl carbonates, alkyl ether carboxylates, fatty acids, sulfosucciates, alkyl ether sulfosuccinates, sarcosinates, octoxynol phosphates, nonoxynol phosphates, taurates, fatty taurides, sulfated monoglycerides, fatty acid amido polyoxyethylene sulfates, and isothienates; or mixtures thereof. Many additional anionic surfactants are described in *McCutcheon's, Detergents and Emulsifiers*, 1993 *Annual*, published by McCutcheon Division, MC Publishing Co., and incorporated herein by reference.

Usually, the anionic surfactant is present in the composition as a neutralized salt in the form of a sodium, potassium, lithium, ammonium, alkylammonium, or hydroxyalkylammonium salt, wherein the alkyl moiety includes one to about three carbon atoms. The alkyl sulfates and alkyl ether sulfates are particularly effective classes of anionic surfactants. Consequently, examples of anionic surfactants useful in the composition and method of the present invention include, but are not limited to, the ammonium, monoethanolamine, diethanolamine, triethanolamine, isopropylamine, sodium, potassium, lithium, or magnesium salt of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or mixtures thereof. Examples of especially useful anionic surfactants are a lauryl sulfate salt, a lauryl ether sulfate salt, a lauryl phosphate, a sulfosuccinate salt, a dodecylsulfonate salt, a cholate salt, a $C_8$ to $C_{18}$ fatty acid, and mixtures thereof.

A test strip of the present invention can be used to assay an undiluted test sample for peroxide or chlorine concentration. Hydrogen peroxide and chlorine are commonly used disinfectants, but most indicator reagent compositions cannot assay undiluted test samples for a high concentration of oxidant because the deep color transitions cannot be differentiated and quantified.

In contrast, a present test strip can be used to assay undiluted test samples for oxidant, either peroxide over the range of 0% to greater than about 4%, and especially about 0.1% to greater than about 4%, by weight, of the composition, or chlorine over the range of 0% to greater than about 1%, and especially about 0.025% to greater than about 1%, by weight, of the composition. This capability greatly increases the versatility of the present test strips because medical workers often use an oxidant to sanitize hemodialysis units. The present test strips, therefore, can be used by medical personnel as a test strip to assay for amounts of sanitizing compound in the working solution.

The carrier for the ingredients of an indicator reagent composition includes water. However, organic solvents, such as acetone, methanol, ethanol, isopropyl alcohol, ethylene glycol, propylene glycol, dimethylformamide, dimethylsulfoxide, acetonitrile, ethyl acetate, and similar solvents, can be included in the carrier vehicle. The selection of a suitable organic solvent or solvents, in addition to water, to include in the carrier of the indicator reagent composition is within the capability of those skilled in the art of designing diagnostic assays.

The amount of organic solvent present in an indicator reagent composition generally is 0% to about 90%, and preferably about 10% to about 70%, by weight of the carrier. A carrier comprising water and an organic solvent, like methanol, ethanol, or acetone, is especially preferred because a carrier matrix impregnated with the indicator reagent composition can be dried within a few to several minutes.

As previously described, an indicator reagent composition undergoes a color transition upon contact with a test sample to provide an assay for peroxide or chlorine concentration from the intensity and degree of the color transition. In accordance with an important feature of the present invention, an indicator reagent composition of the present invention provides a sufficiently resolved and differentiated color transition such that the oxidant in a test sample can be measured and accurately determined without the use of color-measuring instruments, such as spectrophotometers or colorimeters, over a wide concentration range. However, if desired, such color-measuring instruments can be used to measure the difference in color degree and intensity between the test sample and a solution having a known concentration of oxidant.

The intensity and degree of the color transition are used to determine the oxidant content of the test sample by comparing or correlating the color produced by the test sample to colors produced by solutions having a known oxidant concentration. In accordance with an important feature of the present invention, the indicator reagent composition provides a sufficiently resolved and differentiated color transition such that the oxidant content of an undiluted test sample can be measured for test samples having an oxidant content of 0% to greater than about 4%, peroxide, or 0% to greater than 1% chlorine, by weight without the use of color-measuring instruments.

An indicator reagent composition of the present invention, as described above, is used in dry phase, test pad assays for peroxide or chlorine. The dry phase, test pad assay for oxidant utilizing a present indicator reagent composition is performed in accordance with methods well known in the art. In general, the assay for oxidant is performed by contacting the test sample with an analyte detection device that includes an indicator reagent composition. The analyte detection device can be dipped into the test sample, or the test sample can be applied to the analyte detection device dropwise. The resulting change in color of the analyte detection device reveals the oxidant concentration of the test sample; and, if so designed, the resulting color transition can be compared to a standardized color chart to provide a measurement of the oxidant concentration of the test sample.

Typically, the analyte detection device is a test strip impregnated with an indicator reagent composition, designed either as a single pad test strip (to assay only for a single analyte) or as a multiple pad test strip (to assay for several analytes simultaneously). For either type of test strip, the test strip includes a support strip, or handle, normally constructed from a hydrophobic plastic, and a reagent test pad, comprising a bibulous or nonbibulous carrier matrix. In general, the carrier matrix is an absorbent material that allows the test sample to move in response to capillary forces through the matrix to contact the indicator reagent composition and produce a detectable and measurable color transition.

The carrier matrix can be any substance capable of incorporating the chemical reagents required to perform the assay of interest, as long as the carrier matrix is substantially inert with respect to the chemical reagents. The carrier matrix also is porous or absorbent relative to the liquid test sample.

The expression "carrier matrix" refers either to bibulous or nonbibulous matrices that are insoluble in the carrier of the indicator reagent composition and other physiological fluids and that maintain their structural integrity when exposed to the carrier and other physiological fluids. Suitable bibulous matrices include filter paper, sponge materials, cellulose, wood, woven and nonwoven fabrics, and the like. Nonbibulous matrices include glass fiber, polymeric films, and microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulose beads, and especially fiber-containing papers such as filter paper or chromatographic paper; synthetic or modified naturally occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. The carrier matrix can be of different chemical compositions or a mixture of chemical compositions. The matrix also can vary in regards to smoothness and roughness combined with hardness and softness. The handle usually is formed from hydrophobic materials such as cellulose acetate, polyethylene terephthalate, polycarbonate, or polystyrene. The carrier matrix is most advantageously constructed from filter paper or polymeric films.

The carrier matrix of the test strip can be any bibulous or nonbibulous material that allows permeation by the test sample to saturate the test pad of the test strip that is impregnated with the indicator reagent composition. A preferred carrier matrix is a hydrophilic, bibulous matrix, including cellulosic materials, such as paper, and preferably filter paper. The carrier matrix also can be a hydrophilic, nonbibulous matrix, including polymeric films, such as a polyurethane or a crosslinked gelatin. Such polymeric films possess all of the qualities required of a carrier matrix of the present invention, including suspending and positioning both the essential ingredients and any optional ingredients included in the indicator reagent composition, and permeability of the test sample through the carrier matrix.

In accordance with the method of the present invention, to perform a dry phase test strip assay for an oxidant, an aqueous solution, including: (a) about 1% to about 4%, by weight, of an iodide salt; (b) about 0.1% to about 5% by weight of water-soluble polymer, like a cellulose-based polymer; (c) about 1% to about 15% by weight of a buffer; and (d) any other desired optional ingredients, or solvents, first is prepared. A nonbibulous matrix, such as a polyurethane film, or a bibulous matrix, such as filter paper, then is saturated or impregnated with the aqueous solution by immersing or by spraying the aqueous solution onto sheets or precut strips or pads of the polyurethane film or filter paper.

Then, after removing the aqueous solvent by drying in a forced air oven at a temperature of about 40° C. to about 100° C. for about 2 to about 15 minutes, the impregnated polyurethane film or filter paper, if necessary, is cut to an appropriate size, such as a pad having dimensions from about 0.2 in. (inch) (0.5 cm) by about 0.5 in (1.3 cm) to about 0.5 in. (1.3 cm) by about 1 in. (2.5 cm).

It should be understood that it is well within the experimental techniques of those skilled in the art of preparing test devices to determine the proper balance between size of the test pad, the strength of indicator reagent composition solutions, the amount of test sample, and the method of introducing the test sample to the test strip, such as by pipetting rather than dipping, in order to design a quantitative assay for oxidant utilizing the method and composition of the present invention.

The dried, impregnated polyurethane film or filter paper then is secured to an opaque or transparent hydrophobic plastic handle with double-sided adhesive tape. The resulting test strip then is contacted with a test sample for a sufficient time to saturate the test pad with the sample. After waiting a predetermined time, such as from about 1 to about 120 seconds, the test strip is examined, either visually or by instrument, for a response. The color transition, if any, of the test pad reveals the concentration of peroxide or chlorine in the test sample.

In many cases, simple visual observation of the test strip provides the desired information. If more accurate information is required, a color chart bearing color spots corresponding to various known concentrations of oxidant can be prepared for the particular indicator reagent composition used in the test strip. The resulting color of the test strip after contact with the test sample then can be compared with the color spots on the chart to determine the concentration of oxidant in the test sample. If a more accurate determination is required, a spectrophotometer or calorimeter can be used to more precisely determine the degree of the color transition. In addition, the dry phase test strip assay can be made quantitative by employing spectrophotometric or calorimetric techniques, as opposed to visual techniques, in order to more reliably and more accurately measure the degree of color transition, and, therefore, more accurately measure the concentration of oxidant in the test sample.

In accordance with one embodiment of the present invention, the following dry phase test strips were prepared to perform a dry phase assay for peroxide. A strip, a pad, or a sheet of a carrier matrix, like filter paper, such as Whatman 54, available from Whatman Ltd., Maidstone, Kent, U.K., or S&S 404, first was immersed into an aqueous solution containing:

| INDICATOR REAGENT COMPOSITION | |
| --- | --- |
| Ingredient | Amount |
| Water | 18 g (grams) |
| Citrate Buffer 1M (pH 5.5) | 2 g |
| Water-soluble Polymer | 0.2 g |
| Potassium Iodide | 0.5 g |

Excess solution was removed from the surface of the filter paper with a scraper bar.

The impregnated filter paper then was dried in a forced air oven having a temperature of about 60° C. to about 80° C. for about 10 minutes. The dried impregnated filter paper then was backed with a double-sided adhesive, and slit into 0.2 inch (0.5 cm) wide ribbons. A ribbon of filter paper incorporating an indicator reagent composition of the present invention then was attached to a polystyrene plastic support by means of the double-sided adhesive. The plastic support, including the saturated or impregnated filter paper, then was slit into 0.2 inch (0.5 cm) wide strips. Accordingly, the plastic support included a pad having dimensions of about 0.2 inch (0.5 cm) by about 0.2 inch (0.5 cm) of saturated or impregnated filter paper to provide a test pad comprising a filter paper carrier matrix incorporating an indicator reagent composition of the present invention.

To demonstrate the new and unexpected results achieved by the method of the present invention, dry phase test strips incorporating an indicator reagent composition of the present invention were used to assay standardized solutions containing hydrogen peroxide or peracetic acid. Individual test strips, containing different water-soluble polymers, were prepared from the indicator reagent composition described above. Individual strips were dipped into a series of standardized solutions, containing from 0.5% to 3% by weight hydrogen peroxide, or 100 to 2000 ppm peracetic acid.

The test strips also can be used to assay for other peroxides and peracids, such as benzoyl peroxide, performic acid, perbenzoic acid, alkyl and cycloalkyl hydroperoxides having the formula R—OOH, wherein R is an alkyl or cycloalkyl group having one to ten carbon atoms and optionally substituted with a phenyl group, peroxypropanoic acid, peroxybutyric acid, and other peracids having the formula $R_1$—$CO_3H$, wherein $R_1$ is hydrogen, an alkyl or cycloalkyl group containing 1 to 15 carbon atoms, or phenyl.

The standardized solutions were assayed for peroxide by contacting a test strip with a standardized solution for about one (1) second. The color of the test strips then was observed. Timing of the strip reaction is not critical. However, for consistency, the strip color was evaluated after 30 seconds in each test. The test results set forth in Tables 1 and 2 illustrate the difference in color transition provided by different iodide/polymer mixtures to an increasing peroxide concentration. Tables 1 and 2 also show that an iodide/starch mixture provided too intense of a color transition, and, accordingly, quantitative differences in peroxide concentration could not be determined. In each test, the test strip was colorless prior to immersion into a standardized test sample.

TABLE 1

Color response of iodine-polymer complex to increasing hydrogen peroxide concentration

| Polymer | Hydrogen Peroxide Concentration | | | |
|---|---|---|---|---|
| | 0.5% | 1.0% | 2.0% | 3.0% |
| Hydroxypropylcellulose | Yellow | Lt Brown | Brown | Brick |
| Hydroxyethylcellulose | Lt Brown | Brown | Brick | Dk Coffee |
| Carboxymethylcellulose | Brown | Dk Brown | Dk Coffee | Dk Coffee |
| Polyvinylpyrrolidone (PVP) | Y Brown | Brick | Brick | Brick |
| Starch | Bk Blue | Bk Blue | Bk Blue | Bk Blue |

Abbreviations:
Y = yellow,
Lt = light,
Dk = Dark,
Bk = Black

TABLE 2

Color response of iodine-polymer complex to increasing peracetic acid concentration

| Polymer Type | Peracetic Acid Concentration, ppm | | | | | |
|---|---|---|---|---|---|---|
| | 100 | 250 | 500 | 1000 | 1500 | 2000 |
| Hydroxypropylcellulose | Yellow | Y Brown | Brown | Brick | Dk Coffee | Bk Coffee |
| Hydroxyethylcellulose | Y Brown | Lt Brown | Brown | Dk Coffee | Bk Coffee | Bk Coffee |
| Carboxymethylcellulose | Y Brown | Lt Brown | Brown | Dk Coffee | Bk Coffee | Bk Coffee |
| Polyvinylpyrrolidone (PVP) | Y Brown | Lt Brown | Brown | Dk Brown | Dk Brown | Bk Coffee |
| Starch | Bk Blue | Bk Blue | Bk Blue | Bk Blue | Bk Blue | Bk Blue |

The results set forth in Tables 1 and 2 show that a test strip of the present invention is capable of assaying for hydrogen peroxide over the entire range of 0% to greater than 4% by weight, and for peracetic acid over the entire range of 0 to 2000 ppm, by providing a differentiable color response over these entire ranges. Accordingly, a single test strip can be used to assay for a low or a high concentration of peroxide, without diluting the test sample.

In particular, Tables 1 and 2 show that the color transition attributed to an increasing concentration of peroxide varies for different polymers. For example, the hydroxypropylcellulose-iodine complex has a slightly weaker color intensity at higher peroxide concentrations compared to a hydroxyethylcellulose-iodine complex. It was found that using both polymers in an indicator reagent composition in a ratio of about 5:1, for example, gave a more intense color transition and a more differentiable response to a wide range of peroxide concentrations, and especially a high peroxide concentration.

The results summarized in Tables 1 and 2 also show that in the high peroxide concentration range (e.g., about 0.1% by weight or greater) the color differentiation between different peroxide concentrations is relatively easy to distinguish. The color transitions in the high peroxide range are particularly useful in ensuring that hemodialysis units are properly cleaned between patients because the sanitizing solution needed to clean the hemodialysis unit requires a high peroxide concentration.

In another test designed to illustrate the ability of a present indicator reagent composition to quantitatively assay a test sample for a high concentration of peroxide, filter paper was impregnated with potassium iodide, hydroxypropylcellulose, and a buffer, as described above. The impregnated filter paper was used to prepare dry phase test strips. Individual test strips were used to test aqueous solutions containing 0.2% to 4% RENALIN® RENALIN® is a commercial peroxide-based disinfectant solution marketed by Renal Systems, Division of Minntech Corporation, Minneapolis, Minn., and contains about 4% peracetic acid and about 20% hydrogen peroxide. Table 3 summarizes the color response of the test strips to the different concentrations of RENALIN®. All test strips were colorless prior to contact with a RENALIN® solution.

TABLE 3

| RENALIN ® Concentration | Color Transition |
|---|---|
| 0.2% | Yellow |
| 0.5% | Y Brown |
| 1.0% | Lt Brown |
| 2.0% | Brown |
| 3.0% | Brick |
| 3.5% | Dk Brown |
| 4.0% | Bk Brown |

The data summarized in Table 3 show that a dry phase test strip of the present invention can be used in a quantitative assay for peroxide in an aqueous test sample. Table 3 also shows that the assay can be performed on a test sample containing a mixture of peroxides. Prior assays for peracetic acid are based on a starch-iodine complex, and could only determine whether peracetic acid was present in an amount of 500 ppm or greater. These prior tests are unable to provide a quantitative assay for peroxide either above or below 500 ppm.

The above-described test strips also were used to assay for chlorine in a test sample. The chlorine assays were conducted in an identical manner to the above-described peroxide assays. The results summarized in Table 4 show the color differentiation for assays of undiluted test samples containing 250 to 5000 ppm chlorine. Prior assays for chlorine utilizing starch-iodine formed a blue to black color of such intensity that quantitative assays for chlorine concentrations above 200 ppm could not be performed because of a lack of color differentiation between assays of test samples having different chlorine concentrations. The present invention overcomes this problem in assays of undiluted test samples having a relatively high chlorine concentration.

TABLE 4

| Chlorine Concentration | | |
|---|---|---|
| ppm chlorine | % chlorine (by weight) | Color Transition |
| 0 | 0 | colorless |
| 250 | 0.025% | Lt. Yellow |
| 500 | 0.05% | Orange Yellow |
| 1250 | 0.125% | Orange Brown |

TABLE 4-continued

| Chlorine Concentration | | |
|---|---|---|
| ppm chlorine | % chlorine (by weight) | Color Transition |
| 2500 | 0.25% | Brick |
| 5000 | 0.5% | Dark Brown |

An indicator reagent composition of the present invention that includes a water-soluble polymer, in addition to an iodide salt and a buffer to buffer the composition to a pH of about 2 to about 9, therefore, exhibits a sufficiently dramatic color transition, from light yellow to dark brown, to provide a sensitive and accurate assay for peroxide or chlorine in an undiluted test sample. The color transition also is sufficiently resolvable and differentiable, either visually or by instrument, such that an unknown concentration of oxidant in a test sample can be determined.

As previously stated, an important feature of the present invention is to provide a quantitative assay for peroxide in the high detection range of 0.1% by weight or greater, or for chlorine in the high detection range or 0.025% by weight or greater. This was difficult to achieve using prior test strips unless the test sample was diluted to reduce the oxidant concentration to within the detectable range of the test strip. Test sample dilution is undesirable because of the time involved and because of the distinct possibility of dilution error, and, in turn, assay error.

An assay having a broad oxidant detection range allows the user to directly monitor, without dilution, the effective oxidant level of a sanitizing or disinfecting solution. In particular, a 3.5% RENALIN® solution, which commonly is used in hemodialysis operations to sanitize the dialysis system, can be assayed using a present test strip. The problem with currently available test strips is that the detection ranges are either narrow and confined to a specific range or are merely qualitative tests. No present test strip has a detection range to assay for both low, middle, and high concentration levels of oxidant, without dilution of the test sample.

From the visual assays and the data presented in Tables 1–4, it has been demonstrated that an indicator reagent composition of the present invention accurately assays for high levels of peroxide or chlorine, directly and quantitatively, and without test sample dilution. In preferred embodiments, the composition contains a mixture of water-soluble polymers, each having a different response intensity and response range to oxidant levels. If desired, the composition then can be adjusted to detect and measure a specific oxidant range. The color differentiations between different oxidant levels are excellent, therefore, the composition can be used in a quantitative test, rather than a qualitative, positive-negative test.

In accordance with an important feature of the present invention, the continuing and substantial problems in dry phase test strips for quantitatively assaying an undiluted test sample for a high concentration of peroxide or chlorine are essentially eliminated. An indicator reagent composition of the present invention provides a differentiable response to peroxide over the concentration range of 0% to greater than about 4%, and particularly about 0.1% to greater than about 4%, or chlorine over the concentration range of 0% to greater than 1%, and particularly about 0.025% to greater than 1%, by weight of the test sample. Therefore, accurate and reliable assays for oxidant in test samples can be performed by utilizing an indicator reagent composition and device of the present invention.

Obviously, many modifications and variations of the invention as hereinbefore set forth can be made without departing from the spirit and scope thereof, and, therefore, only such limitations should be imposed as are indicated by the appended claims.

What is claimed is:

1. A composition capable of exhibiting a detectable and measurable color transition in response to an oxidant concentration of 0.0% to greater than 4%, by weight, said composition comprising:
(a) an iodide salt;
(b) a buffer;
(c) a water-soluble polymer; and
(d) a carrier comprising water,
wherein the composition has a pH of about 2 to about 9.

2. The composition of claim 1 wherein the oxidant is selected from the group consisting of chlorine, a peroxide, and mixtures thereof.

3. The composition of claim 1 wherein the oxidant is chlorine, and the oxidant concentration is 0% to about 1%, by weight.

4. The composition of claim 3 wherein the chlorine concentration is about 0.025% to about 0.75% by weight.

5. The composition of claim 1 wherein the iodide salt is present in an amount of about 1% to 4%, by weight of the composition.

6. The composition of claim 1 wherein the iodide salt comprises potassium iodide, sodium iodide, lithium iodide, or a mixture thereof.

7. The composition of claim 1 wherein the water-soluble polymer is present in an amount of about 0.1% to about 5%, by weight of the composition.

8. The composition of claim 1 wherein the water-soluble polymer comprises a cellulose-based polymer.

9. The composition of claim 7 wherein the cellulose-based polymer is selected from the group consisting of methylcellulose, hydroxymethylcellulose, hydroxyethylcellulose, hydroxyethylmethylcellulose, hydroxypropylcellulose, hydroxypropylmethylcellulose, carboxymethylcellulose and salts thereof, hydroxybutylcellulose, cellulose acetate, carboxymethylhydroxyethylcellulose, hydroxybutylmethylcellulose, and mixtures thereof.

10. The composition of claim 1 wherein the water-soluble polymer comprises a mixture of cellulose-based polymers.

11. The composition of claim 1 wherein the water-soluble polymer comprises hydroxypropylcellulose.

12. The composition of claim 10 wherein the water-soluble polymer further comprises hydroxyethylcellulose, carboxymethylcellulose, methylcellulose, hydroxymethylcellulose, and mixtures thereof.

13. The composition of claim 1 wherein the water-soluble polymer comprises polyvinylpyrrolidone, hydrolyzed polyvinylpyrrolidone, poly-(vinyl alcohol), poly(vinyl acetate), a vinyl acetate-vinyl alcohol copolymer, polyvinyloxazolidone, polyvinylmethyloxazolidone, a copolymer of vinylpyrrolidone and a vinyl amide of γ-amine butyric acid, a polyacrylic acid polymer, a polyacrylic acid copolymer, a partially or fully neutralized salt of a polyacrylic acid polymer or a polyacrylic acid copolymer, poly (methacrylic acid), poly(methacrylamide), poly(N,N-dimethylacrylamide), poly(N-isopropylacrylamide), poly (N-acetamidoacrylamide), poly(N-acetamidomethacrylamide), an acrylic interpolymer of polyacrylic acid with poly(methacrylic acid), polyacrylic acid with poly(methacrylamide), polyacrylic acid with methacrylic acid, a polyoxypropylene-polyoxyethylene block polymer having a structure:

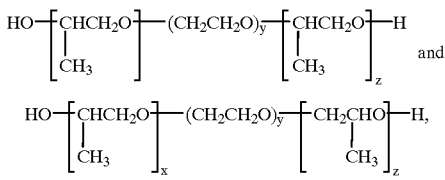
and wherein x and z, independently, are an integer from about 4 to about 30, and y is an integer from about 4 to about 100, polyacrylamide, a copolymer of acrylamide, an acrylamide/sodium acrylate copolymer, an acrylate/acrylamide copolymer, an acrylate/ammonium methacrylate copolymer, an acrylate/diacetoneacrylamide copolymer, an acrylic/acrylate copolymer, an adipic acid/dimethylaminohydroxypropyl diethylenetriamine copolymer, an ammonium acrylate copolymer, an ammonium styrene/acrylate copolymer, an ammonium vinyl acetate/acrylate copolymer, an aminomethylpropanol acrylate/diacetoneacrylamide copolymer, an aminomethylpropanediol acrylate/diacetoneacrylamide copolymer, a butyl benzoic acid/phthalic anhydride/trimethylolethane copolymer, a diethylene glycolamine/epichlorohydrin/piperazine copolymer, an ethylene/vinyl alcohol copolymer, an ethyl ester of polyethylenimine, an isopropyl ester of methyl vinyl ether/maleic anhydride copolymer, a melamine/formaldehyde resin, a methoxyethylene glycol/dodecyl glycol copolymer, an octadecene/maleic anhydride copolymer, an octylacrylamide/acrylate/butylaminoethyl methacrylate copolymer, an octylacrylamide/acrylate copolymer, a polyethylene glycol/dodecyl glycol copolymer, a polyethyleneimine, phthalic anhydride/glycerin/glycidyl decanoate copolymer, a metal salt of polyacrylic acid, a metal salt of a methyl vinyl ether/maleic anhydride copolymer, a vinylpyrrolidone/eicosene copolymer, a vinylpyrrolidone/ethyl methacrylate/methacrylic acid copolymer, a vinylpyrrolidone/hexadecene copolymer, a vinylpyrrolidone/vinyl acetate copolymer, a polyvinylpyrrolidone/vinyl acetate/itaconic acid copolymer, a sodium acrylate/vinyl alcohol copolymer, sodium polymethacrylate, sodium polystyrene sulfonate, a sodium styrene/acrylate/polyethylene glycol-10 dimaleate copolymer, a sodium styrene/polyethylene glycol-10 maleate/nonoxynol-10 maleate/acrylate copolymer, a styrene/acrylamide copolymer, a styrene/acrylate/ammonium methacrylate copolymer, a styrene/maleic anhydride copolymer, a styrene/polyvinyloxazolidone copolymer, a urea formaldehyde polymer, a urea/mel-amine/formaldehyde polymer, a vinyl acetate/crotonic acid copolymer, a vinyl alcohol copolymer, and mixtures thereof.

14. The composition of claim 13 wherein the water-soluble polymer further comprises a cellulose-based polymer.

15. The composition of claim 13 wherein the water-soluble polymer further comprises a mixture of cellulose-based polymers.

16. The composition of claim 1 wherein the buffer is present in an amount of about 1% to about 15%, by weight of the composition.

17. The composition of claim 1 wherein the buffer is selected from the group consisting of a polycarboxylic acid wherein the carboxyl groups are separated by two to five carbon atoms, citric acid, succinic acid, ketoglutaric acid, lactic acid, phosphate, borate, acetate, and mixtures thereof.

18. The composition of claim 1 wherein the composition has a pH of about 4 to about 7.

19. The composition of claim 1 further comprising an anionic or a nonionic surfactant in an amount of 0% to about 1.5% by weight of the composition.

20. The composition of claim 19 wherein the nonionic surfactant is selected from the group consisting of an ethoxylated polysorbate, an ethoxylated alcohol, an ethoxylated phenol, a polyethylene glycol, a polypropylene glycol, an ethylene glycol-propylene glycol copolymer, a polybutylene glycol, and mixtures thereof.

21. The composition of claim 19 wherein the anionic surfactant comprises a sulfate, a sulfonate, a carbonate, a phosphate, or a carboxylate.

22. The composition of claim 19 wherein the anionic surfactant is selected from the group consisting of an alkyl sulfate, an alkyi ether sulfate, an alkyl ether sulfonate, a sulfate ester of an alkylphenoxy polyoxyethylene ethanol, an alphaolefin sulfonate, a beta-al-kyloxy alkane sulfonate, an alkyl arylsulfonate, an alkyl carbonate, an alkyl ether carboxylate, a fatty acid, a sulfosuccinate, an alkyl ether sulfosuccinate, a sarcosinate, an octoxynol phosphate, a nonoxynol phosphate, a taurate, a fatty tauride, a sulfated monoglyceride, a fatty acid amido polyoxyethylene sulfate, and mixtures thereof.

23. The composition of claim 1 wherein the carrier comprises 0% to about 90% by weight of the carrier of an organic solvent.

24. The composition of claim 1 comprising:
(a) about 1.5% to about 3% by weight potassium iodide;
(b) about 5% to about 12% by weight of a buffer selected from the group consisting of a polycarboxylic acid having carboxyl groups separated by two to five carbon atoms;
(c) about 0.2% to about 3% by weight of hydroxypropylcellulose, hydroxyethylcellulose, methylcellulose, hydroxymethylcellulose, carboxymethylcellulose, polyvinylpyrrolidone, and mixtures thereof; and
(d) a carrier comprising water,
wherein the composition has a pH of about 5 to about 6.5.

25. The composition of claim 24 comprising about 0.2% to about 2.5% by weight of a mixture of hydroxypropylcellulose, hydroxyethylcellulose, and polyvinylpyrrolidone.

26. A method of determining a chlorine content of an aqueous test sample containing 0 to 10,000 ppm chlorine, said method comprising:
(a) contacting the aqueous test sample with an indicator reagent composition comprising:
(i) an iodide salt,
(ii) a buffer,
(iii) a water-soluble polymer, and
(iv) a carrier comprising water,
(b) determining the chlorine content of the aqueous test sample from the intensity and degree of a color transition of the indicator reagent composition.

27. The method of claim 26 wherein the aqueous test sample has a chlorine content of about 200 to about 7500 ppm.

28. The method of claim 26 wherein the aqueous test sample has a chlorine content of about 250 to about 5000 ppm.

29. The method of claim 26 wherein the aqueous test sample is an undiluted test sample.

30. The method of claim 26 wherein the intensity and degree of the color transition are determined visually or instrumentally.

31. A method of quantitatively determining the oxidant content of an aqueous sample containing 0 to about 10,000 ppm oxidant, said method comprising:
  (a) contacting the aqueous sample with an analyte detection device comprising a test pad, said test pad having incorporated therein an indicator reagent composition comprising:
    (i) an iodide salt,
    (ii) a buffer,
    (iii) a water-soluble polymer, and
    (iv) a carrier comprising water,
  (b) determining the oxidant content of the aqueous sample from the intensity and degree of a color transition of the indicator reagent composition.

32. The method of claim 31 wherein the oxidant is chlorine, a peroxide, or a mixture thereof.

33. A method of determining the oxidant content of an aqueous sample comprising:
  (a) contacting the aqueous sample with an analyte detection device comprising a test pad having incorporated therein:
    (i) an iodide salt,
    (ii) a buffer,
    (iii) a water-soluble polymer, and
    (iv) a carrier comprising water,
  (b) examining the analyte detection device for a color transition; and
  (c) correlating the color transition to the oxidant content of the aqueous sample.

34. The method of claim 33 wherein the aqueous sample has an oxidant content of 0 to about 10,000 ppm chlorine.

* * * * *

UNITED STATES PATENT AND TRADEMARK OFFICE
CERTIFICATE OF CORRECTION

PATENT NO. : 6,087,089
DATED : July 11, 2000
INVENTOR(S) : Wen H. Wu

It is certified that error appears in the above-identified patent and that said Letters Patent is hereby corrected as shown below:

Column 18, line 9, replace "0.00%" with "0%".

Column 18, line 21, replace "chiorine" with "chlorine".

Column 19, line 6, replace "and" between the two chemical formulas with "or".

Column 20, line 16, replace "alkyi" with "alkyl".

Column 20, line 18, delete the "dash" between "beta-al" and "kyloxy".

Signed and Sealed this

Twenty-second Day of May, 2001

Attest:

NICHOLAS P. GODICI

Attesting Officer

Acting Director of the United States Patent and Trademark Office